(12) United States Patent
Singh et al.

(10) Patent No.: US 8,993,019 B2
(45) Date of Patent: Mar. 31, 2015

(54) EMULSION

(75) Inventors: Harjinder Singh, Palmerston North (NZ); Aiqian Ye, Palmerston North (NZ); Xiang-Qian Zhu, Palmerston North (NZ)

(73) Assignee: Massey University (NZ)

( * ) Notice: Subject to any disclaimer, the term of this patent is extended or adjusted under 35 U.S.C. 154(b) by 223 days.

(21) Appl. No.: 13/643,447

(22) PCT Filed: Apr. 26, 2011

(86) PCT No.: PCT/NZ2011/000055
§ 371 (c)(1),
(2), (4) Date: Jan. 4, 2013

(87) PCT Pub. No.: WO2011/136662
PCT Pub. Date: Nov. 3, 2011

(65) Prior Publication Data
US 2013/0115258 A1    May 9, 2013

(30) Foreign Application Priority Data
Apr. 26, 2010 (NZ) ........................ 584896

(51) Int. Cl.
| | | |
|---|---|---|
| *A61B 17/22* | (2006.01) | |
| *A61K 9/00* | (2006.01) | |
| *A61B 18/18* | (2006.01) | |
| *A61K 8/06* | (2006.01) | |
| *A23C 9/152* | (2006.01) | |
| *A23D 7/005* | (2006.01) | |
| *A23D 7/06* | (2006.01) | |
| *A23L 1/22* | (2006.01) | |
| *A23L 1/30* | (2006.01) | |
| *A23L 1/305* | (2006.01) | |

(52) U.S. Cl.
CPC .................. *A61K 8/062* (2013.01); *A23C 9/152* (2013.01); *A23C 9/1528* (2013.01); *A23D 7/0053* (2013.01); *A23D 7/06* (2013.01); *A23L 1/22058* (2013.01); *A23L 1/3008* (2013.01); *A23L 1/3055* (2013.01); *A23L 1/3056* (2013.01); *A23V 2002/00* (2013.01)

USPC ............... 426/89; 426/601; 606/45; 606/128; 424/400

(58) Field of Classification Search
USPC ..................................... 426/89, 601
See application file for complete search history.

(56) References Cited

U.S. PATENT DOCUMENTS

| | | | |
|---|---|---|---|
| 4,895,725 A | 1/1990 | Kantor et al. | |
| 5,160,759 A | 11/1992 | Nomura et al. | |
| 7,374,788 B2 | 5/2008 | Augustin et al. | |
| 2007/0141223 A1 | 6/2007 | Moore et al. | |
| 2008/0299200 A1 | 12/2008 | Leser et al. | |
| 2008/0299281 A1 | 12/2008 | Burger | |
| 2009/0029017 A1 | 1/2009 | Singh et al. | |
| 2010/0172831 A1* | 7/2010 | Mason et al. | ................. 424/1.29 |

FOREIGN PATENT DOCUMENTS

| | | |
|---|---|---|
| EP | 0 255 660 A1 | 2/1988 |
| GB | 1 440 182 A | 6/1976 |
| JP | 60-102168 A | 6/1985 |
| JP | 07-087889 A | 4/1995 |
| JP | 2006-328254 A | 12/2006 |
| WO | WO 96/19114 A1 | 6/1996 |
| WO | WO 01/80656 A1 | 11/2001 |
| WO | WO 2006/115420 A1 | 11/2006 |

OTHER PUBLICATIONS

International Search Report for corresponding International Patent Application No. PCT/NZ2011/000055 mailed Jul. 13, 2011.

* cited by examiner

*Primary Examiner* — Gina Justice
*Assistant Examiner* — Genevieve S Alley
(74) *Attorney, Agent, or Firm* — Merchant & Gould P.C.

(57) ABSTRACT

The invention relates to the encapsulation of oxidizable lipids. In particular, the invention provides an oil-in-water emulsion comprising droplets of a core lipid coated with nanoemulsion droplets, wherein the nanoemulsion droplets comprise a surface lipid coated with protein. The emulsions of the invention provide an oxidatively stable form of the lipid, which can be added to foods and cosmetics requiring a long shelf-life.

15 Claims, 9 Drawing Sheets

EMULSION

Figure 1:
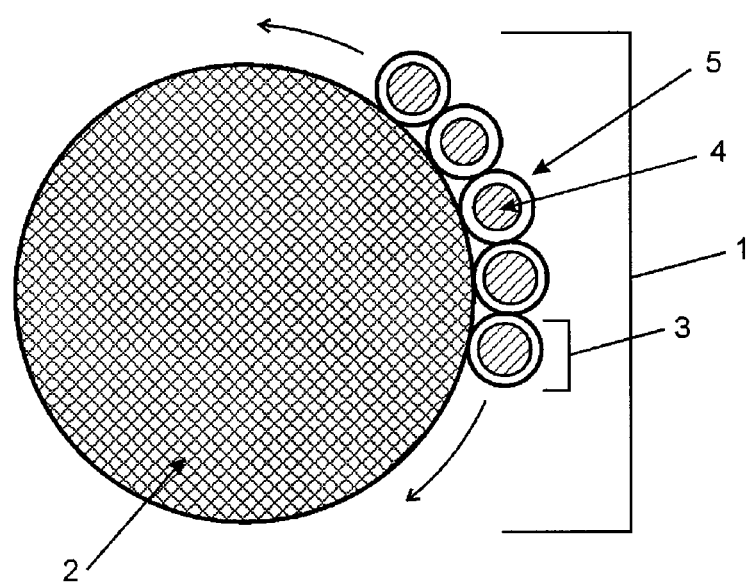

This application is a U.S. National Stage Application under 35 U.S.C. §371 of International Patent Application No. PCT/NZ2011/000055, filed 26 Apr. 2011, which claims the benefit of priority to New Zealand Patent Application No. 584896, filed 26 Apr. 2010, the disclosures of all of which are hereby incorporated by reference in their entireties. The International Application was published in English on 3 Nov. 2011 as WO 2011/136662.

1. FIELD OF THE INVENTION

This invention relates to the encapsulation of lipids, in particular, oxidisable lipids. The invention relates to an oil-in-water emulsion that protects the lipid phase of the emulsion from oxidative damage by coating the lipids with nanoemulsion droplets. The nanoemulsion droplets comprise a surface lipid coated with protein. The invention also provides a method of preparing the emulsion, and foods and cosmetics containing the emulsion.

2. BACKGROUND

It is now established that long chain polyunsaturated fatty acids (LC PUFAs) provide extensive nutritional and health benefits in human health (Uauy-Dagach, R. and Valenzuela, A. Nutrition Reviews 1996; 54, 102-108; Ruxton, C. H. S., Reed, S. C., Simpson, J. A. and Millington, K. J. 2004; J. Human Nutr. Dietet. 17, 449-459).

For example, omega-3 LC PUFAs have been documented as contributing to the prevention of coronary heart disease, hypertension, type 2 diabetes, rheumatoid arthritis, Crohn's disease and obstructive pulmonary disease (Simopoulos A P, Am J Clin Nutr, 1999; 70:560-569).

Recognition of the potential benefits of these lipids has stimulated interest in foods and nutraceuticals that contain them. Fish oil is a predominant dietary source of omega-3 LC PUFA. However, the average fish intake is currently far below the recommended 2-3 fish servings per week. Fortification of various foods with fish oil is an innovative way of elevating the intake of omega-3 LC PUFA without necessitating radical changes in eating habits. However, incorporating lipids such as omega-3 LC PUFA into food products gives rise to major formulation challenges.

Like many lipids, LC PUFAs are sensitive to heat, light and oxygen and undergo oxidative damage very quickly. Fatty acid oxidation is a major cause of food deterioration which can affect the flavour, aroma, texture, shelf life and colour of food.

Besides producing undesirable characteristics in the food such as off-flavour, oxidative damage can eliminate the beneficial biological activity of a lipid. There is also a potential for health damage by increasing free radical formation in the body. Accordingly, if oxidisable lipids such as omega-3 fatty acids are to be successfully incorporated into food products, these negative characteristics must be avoided.

One way of reducing oxidative damage is to encapsulate the lipid so as to reduce its contact with oxygen, trace metals and other substances that attack the double bonds and other susceptible locations of the lipid. To this end, oxidisable lipids have been encapsulated by a number of other substances including polysaccharides and proteins, often in the form of an oil-in-water emulsion. The other substances act as emulsifiers, stabilising the interface between the lipid droplets and the water phase.

In U.S. Pat. No. 4,895,725 microcapsules of fish oil are produced by encapsulating the oil within a non-oil soluble enteric coating. Although palatable, the resulting capsules are not heat stable and are unstable at a pH higher than 7. This greatly limits their application in a wide range of food products.

Proteins have also been used to encapsulate oxidisable lipids and have been partially successful in reducing the odour of strong smelling lipids. For example; Patent Application JP 60-102168 describes a fish oil emulsion incorporating hydrophilic proteins that is able to at least partially suppress the fishy smell. However, the composition is vulnerable to oxidation and must still contain an antioxidant. Oxidation mechanisms in complex food systems are different from those in bulk oils. Compounds that are efficient antioxidants in a bulk oil may have pro-oxidant activity in complex food systems. It may therefore be desirable to avoid or minimise incorporation of antioxidant compounds in some situations.

PCT publication WO 01/80656 describes a composition that comprises a milk or aqueous portion, a protecting oil such as oat oil or oat bran oil and one or more PUFAs stabilised with soy protein. The emulsion is reported to demonstrate a lower oxidation rate than an unstabilised emulsion because of the antioxidant properties of the protecting oil.

PCT publication WO 96/19114 describes a water-in-oil emulsion containing a fish oil. The lipid phase of the emulsion comprises unhydrogenated fish oil and an antioxidant. The aqueous phase must not contain any ingredient that can react or catalyse a reaction with the components of the fat phase. The specification reports that milk proteins contain ingredients which may react with or act as catalysts for a reaction with the fish oil and/or antioxidant causing a metallic off-flavour or fishy taste. It is therefore suggested that the use of these proteins in the emulsion is to be avoided.

Milk proteins have, however, been used in combination with carbohydrates to encapsulate oxygen-sensitive oils in U.S. Pat. No. 7,374,788. The specification describes heating a milk protein such as casein, soy or whey with a carbohydrate containing a reducing group. The resulting Maillard reaction products are mixed with the oil and homogenised. Unfortunately, Maillard reaction products are considered to have a negative effect on human health. In addition, the high sugar content of the resulting emulsion precludes its use in low calorie and/or low carbohydrate savoury products.

WO 2006/115420 describes the use of a complex of casein and whey protein to encapsulate oxidisable oils such as fish oils. While this complex protects the fish oil from oxidation, there is still a need to provide an oil-in-water fish oil emulsion with demonstrable long term shelf stability.

Consequently, it is an object of the invention to provide an improved or alternative emulsion for encapsulating lipids that alleviates at least some of the disadvantages discussed above, or at least provides the public with a useful choice.

3. SUMMARY OF INVENTION

The invention relates to an oil-in-water emulsion comprising droplets of a core lipid coated with nanoemulsion droplets, wherein the nanoemulsion droplets comprise a surface lipid coated with protein.

The invention also relates to an oil-in-water emulsion comprising droplets of a core lipid coated with nanoemulsion droplets, wherein the nanoemulsion droplets comprise a surface lipid coated with protein, wherein the oil-in-water emulsion has high oxidative stability relative to an oil-in-water emulsion comprising equivalent amounts of homogenised core lipid, surface lipid and protein, wherein oxidative stability is measured using one or more of the TBARS, PV or propanal determinations.

The invention also relates to an oil-in-water emulsion comprising droplets of a core lipid coated with nanoemulsion droplets, wherein the nanoemulsion droplets comprise a surface lipid coated with protein, wherein the oil-in-water emulsion is oxidatively stable following heat treatment.

In another aspect the invention relates to a method of making an emulsion of the invention comprising
 (a) homogenising a surface lipid with a solution of protein to produce a nanoemulsion comprising droplets of the surface lipid coated with protein,
 (b) homogenising the nanoemulsion with a core lipid to produce an emulsion comprising droplets of core lipid coated with nanoemulsion droplets,
wherein the nanoemulsion droplets comprise the surface lipid coated with protein.

In another aspect the invention relates to a food or cosmetic product comprising an emulsion of the invention.

In the above aspects of the invention:

In one embodiment the core lipid comprises an oxidisable lipid, for example, a LC PUFA or ester thereof. Preferably, the core lipid comprises a highly unsaturated fatty acid or ester thereof. In one embodiment, the core lipid is a plant oil or fish oil or is derived from plant or fish oil. Most preferably, the core lipid comprises an omega-3 fatty acid, such as α-linolenic acid (ALA), eicosapentaenoic acid (EPA) or docosahexaenoic acid (DHA), or combination thereof.

In one embodiment the surface lipid is a lipid that is solid or partially solid at room temperature. Preferably the surface lipid is a non-oxidisable lipid. More preferably the surface lipid is selected from the group comprising palm oil, anhydrous milk fat, coconut oil, cocoa butter and hydrogenated or partially hydrogenated vegetable oils (for example, soybean, rapeseed, sunflower, peanut, cottonseed, olive, corn, grape seed, safflower, sesame, rice bran, and linseed oils) and mixtures thereof.

In one embodiment, the oil-in-water emulsion comprises about 5-40%, 10-30%, preferably about 20% core lipid. In another embodiment, the oil-in-water emulsion comprises about 2 to 30% surface lipid, preferably about 6 to 14%, more preferably about 10% surface lipid.

In one embodiment the protein is a milk protein. In one embodiment, the protein is selected from the group comprising MPC, MPI, WPI, whey protein, skim milk powder, casein, sodium caseinate, soy protein, egg protein, calcium caseinate or aggregates derived from these proteins or mixtures thereof.

In one embodiment the nanoemulsion droplets have an average diameter of about 50 to 1000 nm. Preferably the average diameter of the nanoemulsion droplets is 50 to 500 nm, more preferably, 50 to 200 nm.

In one embodiment, the nanoemulsion droplets coating the core lipid form a layer 50 to 500 nm thick, preferably 50 to 300 nm, more preferably 100 to 200 nm thick.

In one embodiment the core lipid droplets have an average diameter of about 1000 nm to 100 μm, preferably 2 to 50 μm, more preferably 5 to 10 μm.

In one embodiment the food product is a dairy product including but not limited to milk or milk-based products, yogurts and cheeses.

In one embodiment the invention provides an oil-in-water emulsion comprising droplets of fish oil coated with nanoemulsion droplets, wherein the nanoemulsion droplets comprise a lipid that is solid or partially solid at room temperature, the surface lipid being coated with a milk protein.

In another embodiment the invention provides an oil-in-water emulsion comprising droplets of fish oil coated with nanoemulsion droplets, wherein the nanoemulsion droplets comprise one or more surface lipids selected from the group comprising palm oil, partially or fully hydrogenated vegetable oil and milk fat, the surface lipid being coated with a milk protein.

In another embodiment the invention provides an oil-in-water emulsion comprising droplets of fish oil coated with nanoemulsion droplets, wherein the nanoemulsion droplets comprise a lipid that is solid or partially solid at room temperature, the surface lipid being coated with a milk protein; wherein the oil-in-water emulsion comprises about 10 wt % fish oil and 6-14 wt % surface lipid.

In another embodiment the invention relates to an oil-in-water emulsion comprising droplets of fish oil coated with nanoemulsion droplets, wherein the nanoemulsion droplets comprise a lipid that is solid or partially solid at room temperature, the surface lipid being coated with milk protein; wherein the fish oil droplets have an average diameter of about 2 to about 5 μm and the nanoemulsion droplets have an average diameter of about 50 to about 500 μm.

In another aspect the invention relates to a method of making yogurt fortified with an oxidisable lipid comprising
 (a) adding to milk and yogurt culture, an emulsion of the invention wherein the core lipid comprises an oxidisable lipid,
 (b) heat treating the mixture formed in step (a), and
 (c) fermenting the mixture of step (b) to produce a yogurt fortified with oxidisable lipid.

In one embodiment the oxidisable lipid comprises a LC PUFA or ester therefore. Preferably the oxidisable lipid comprises a plant oil or fish oil. Most preferably, the oxidisable lipid comprises an omega-3 fatty acid, such as α-linolenic acid (ALA), eicosapentaenoic acid (EPA) or docosahexaenoic acid (DHA), or combination thereof.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

4. BRIEF DESCRIPTION OF THE DRAWINGS

The invention will now be described with reference to the drawings in which:

FIG. 1: A schematic representation of a particle of the emulsion of the invention.

Figure 2:
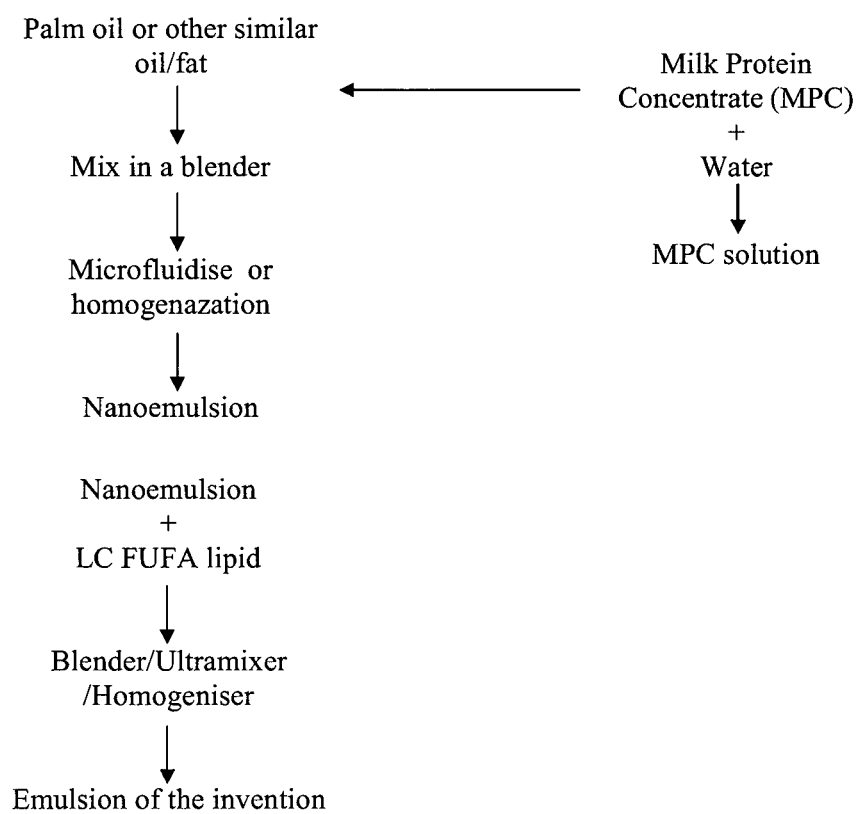

FIG. 2: A diagram showing the method of making the emulsions of the invention

Figure 3:
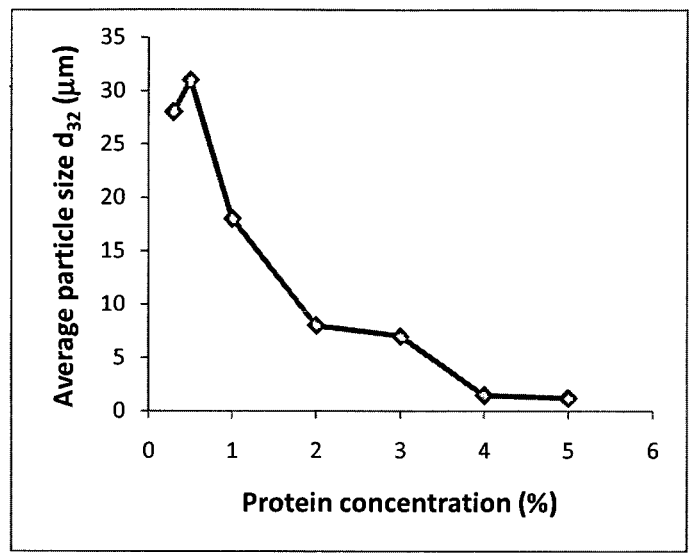

FIG. 3: A graph showing the particle size of the emulsions made with 20% (w/w) palm oil and MPC solution homogenized at 250/50 bars (25/5 MPa), as a function of MPC concentration.

Figure 4:
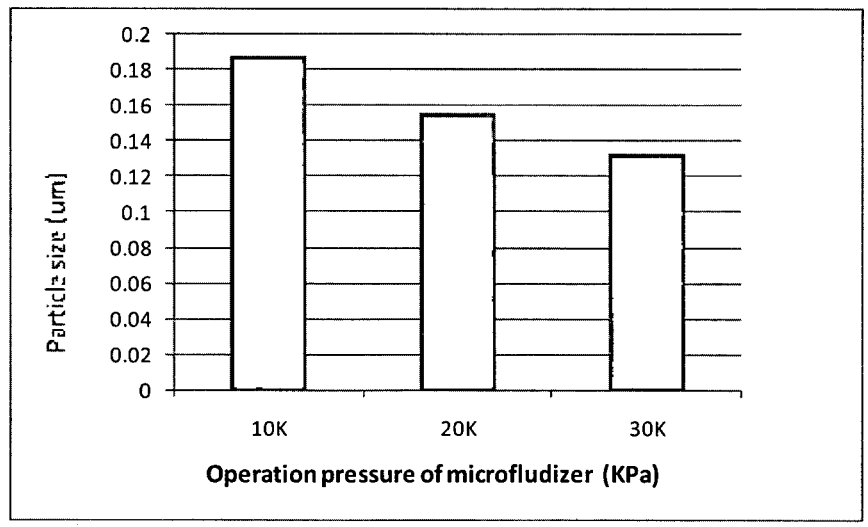

FIG. 4: A graph showing the particle size of nanoemulsions made with 20% (w/w) palm oil and 4% (w/w) MPC solution homogenized using a microfludizer at different pressures.

Figure 5:
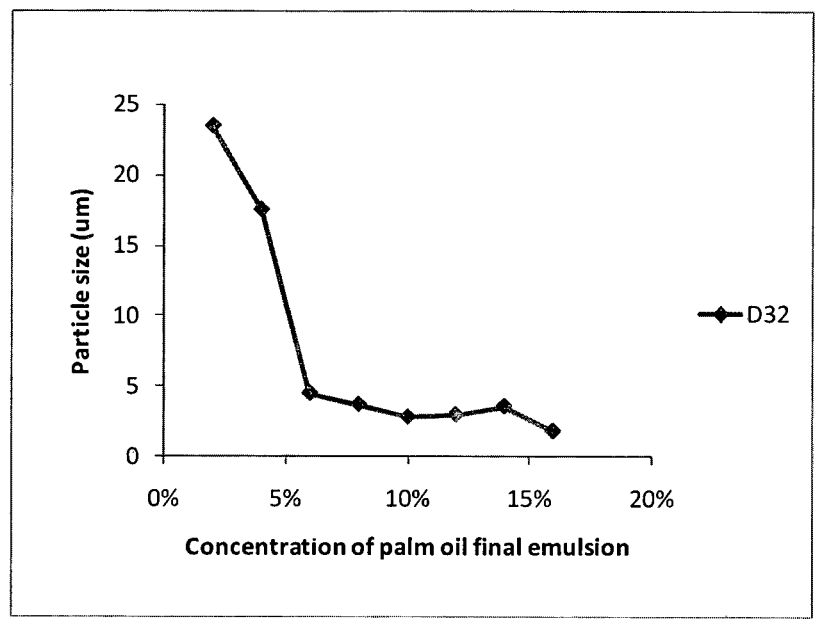

FIG. 5: The particle size of emulsions of the invention as a function of the nanoemulsion concentration.

Figure 6:

FIG. 6: A confocal micrograph of the emulsion of the invention.

Figure 7:
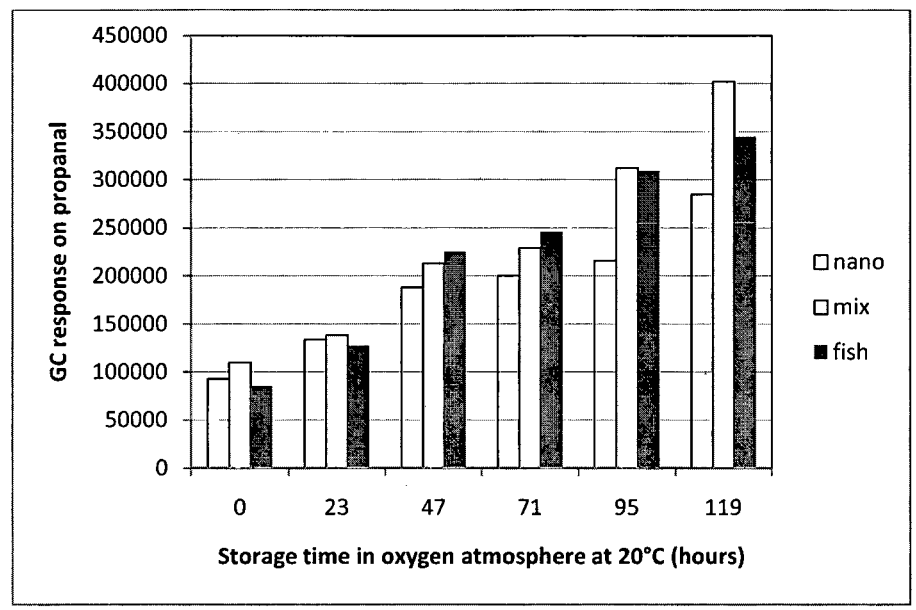

FIG. 7: A graph showing the headspace propanal in emulsions of the invention (nano) (□), mix emulsion (■) and fish oil emulsion (■).

Figure 8:
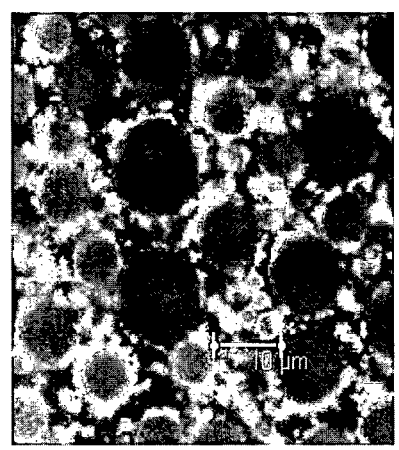

FIG. 8: Confocal micrograph of an emulsion of the invention made with 20% (w/w) fish oil and 10% (w/w) nanoemulsion formed by 4% (w/w) MPC solution and 20% (w/w) sunflower oil.

Figure 9:
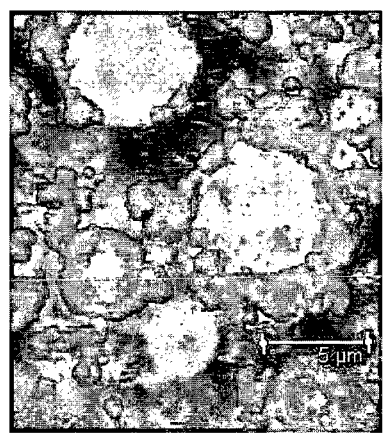

FIG. 9: Confocal micrograph of an emulsion of the invention droplets made with 20% (w/w) fish oil and 10% (w/w) nanoemulsion formed by 4% (w/w) MPC solution and 20% (w/w) milk fat.

Figure 10:
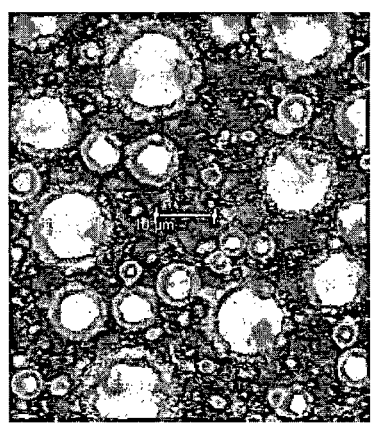

FIG. 10: Confocal micrograph of an emulsion of the invention made with 20% (w/w) fish oil and 5% (w/w) nanoemulsion formed by 15% (w/w) SMP solution and 20% (w/w) palm oil.

Figure 11:
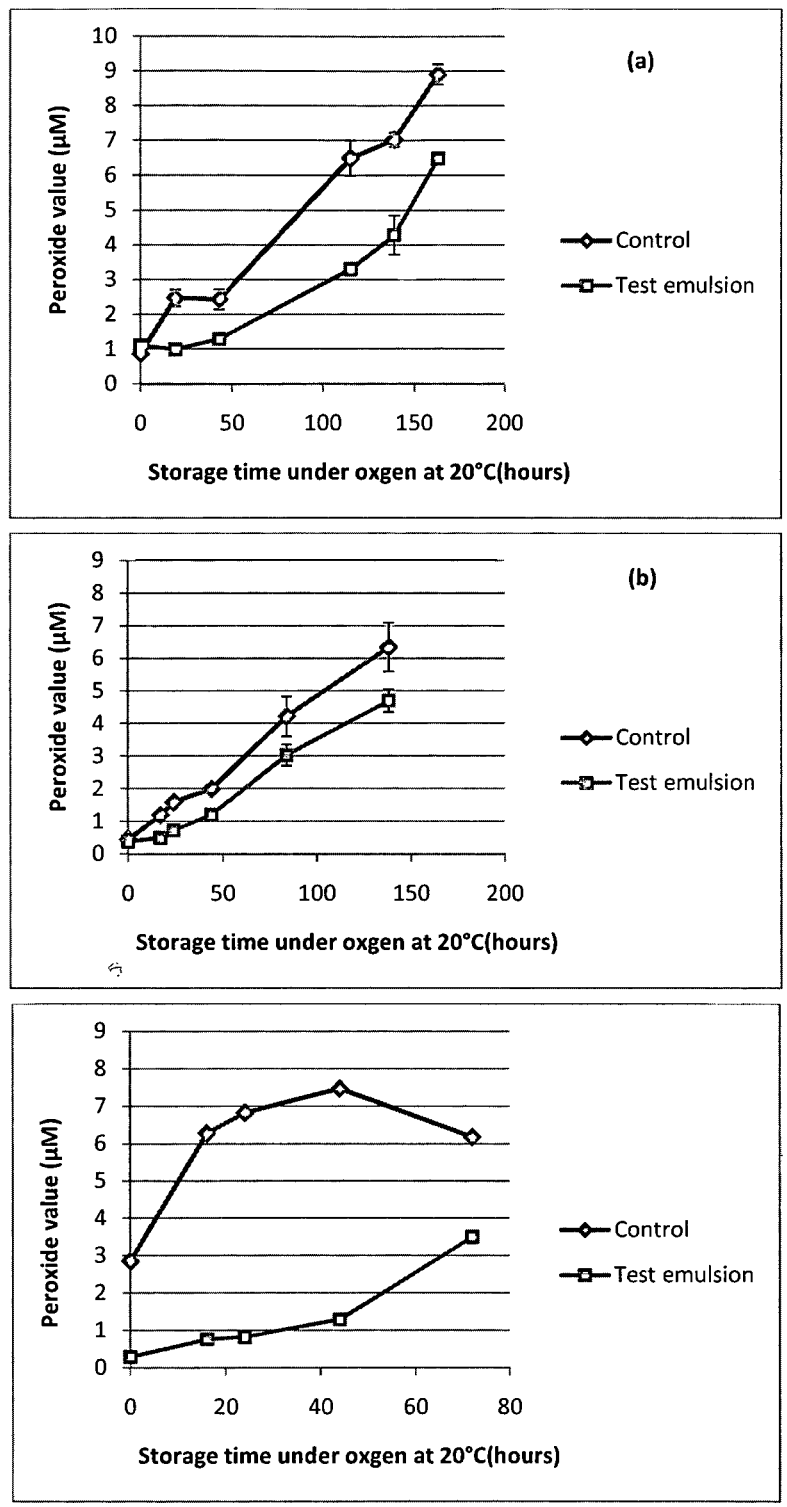

FIG. 11: Graphs showing the Lipid hydroperoxide values of control samples and emulsions of the invention made with different surface lipids: (a) palm oil, (b) high melting point anhydrous milk fat, and (c) high melting point vegetable oil. The graphs show the peroxide value after storage under oxygen at 20° C.

Figure 12:
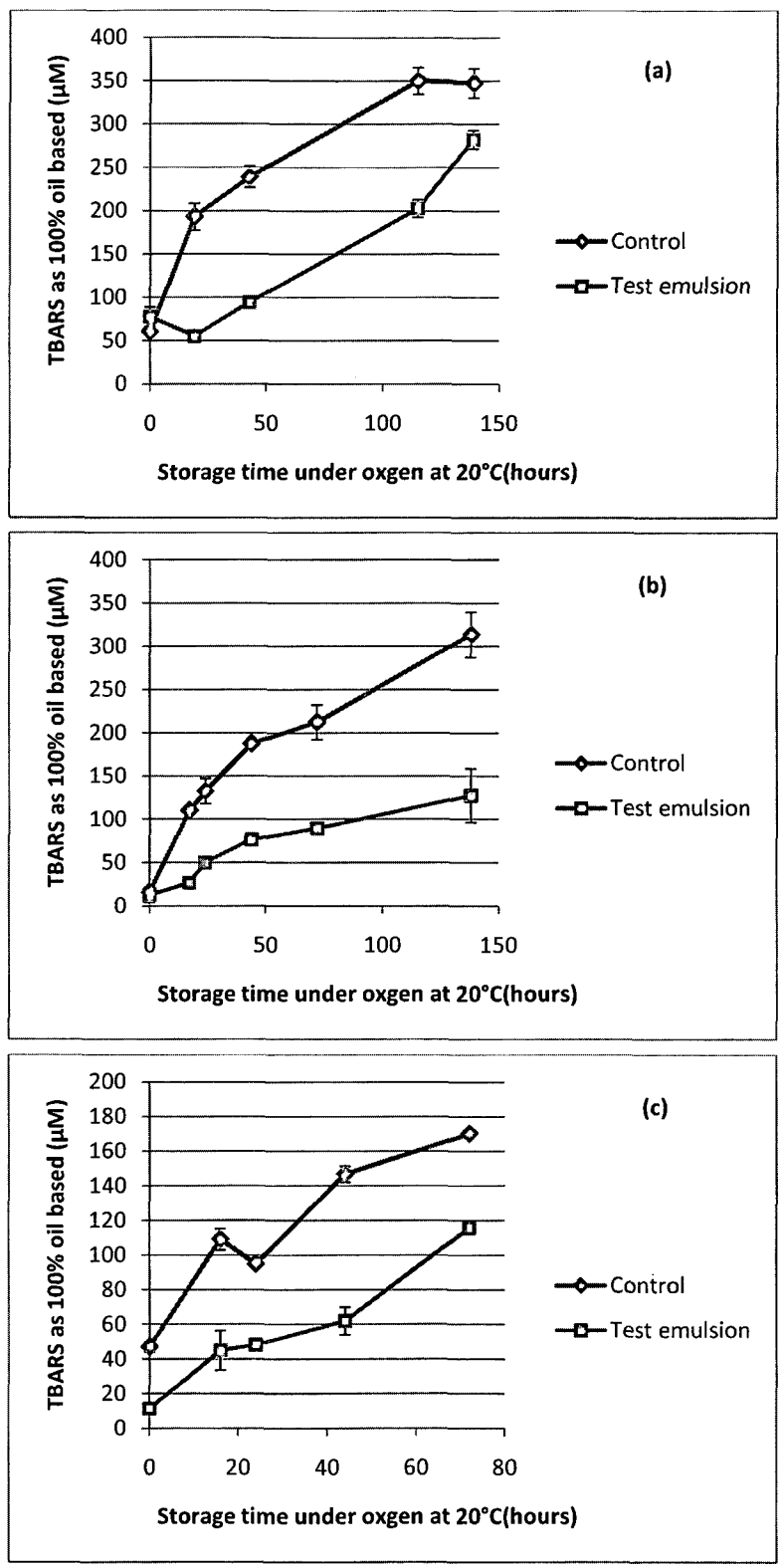

FIG. 12: Graphs showing the thiobarbituric acid reactive substances (TBARS) values of control samples and emulsions of the invention made with different surface lipids: (a) palm oil, (b) high melting point milk, and (c) high melting point vegetable lipid. The graphs show the peroxide value after storage under oxygen at 20° C.

Figure 13:
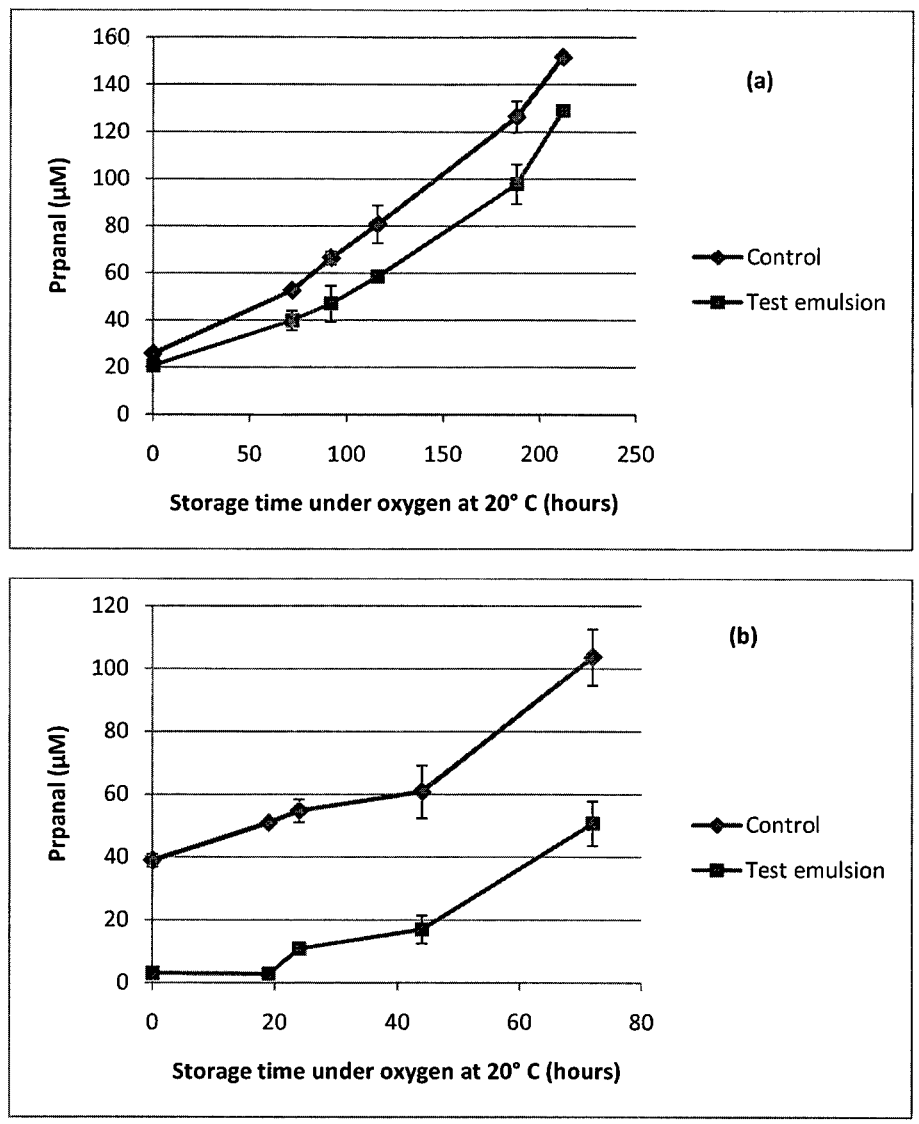

FIG. 13: Graphs showing the Propanal values of control samples and emulsions of the invention made with different surface lipids: (a) palm oil, and (b) high melting point vegetable oil.

5. DETAILED DESCRIPTION OF THE INVENTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

5.1 Definitions

The term "milk protein concentrate" (MPC) as used herein refers to a milk protein product in which greater than 55%, preferably greater than 75%, of the solids-not-fat (SNF) is milk protein and the ratio of casein to whey proteins is between 98:2 and 50:50, preferably between 90:10 and 70:30, most preferably between 90:10 and 80:20. Such concentrates are known in the art. MPCs are frequently described with the % dry matter as milk protein being appended to "MPC". For example MPC70 is an MPC with 70% of the dry matter as milk protein. While MPCs are generally prepared without use of non-dairy ingredients, they may also contain additives such as non-dairy fat including vegetable fat.

The term "milk protein isolate" (MPI) as used herein refers to a milk protein composition comprising a substantially unaltered proportion of casein to whey proteins wherein the dry matter consists of greater than 85% milk protein. Such isolates are known in the art.

The term "whey protein isolate" (WPI) as used herein is a whey fraction in which at least 90% (w/w) of the total solids comprise whey proteins. WPIs are generally prepared by microfiltration or ion exchange in combination with ultrafiltration and/or diafiltration of whey. Again, the protein composition is preferably substantially that of the whey from which it was derived. WPIs can be in the form of liquid concentrates or dried powders.

The term "lipid" as used herein means a substance that is soluble in organic solvents and includes, but is not limited to, oils, fats, triglycerides, fatty acids and esters, phospholipids, sphingolipids and sterol lipids.

The term "emulsion" as used herein means a composition comprising two immiscible liquid phases wherein one of the liquid phases is dispersed in the other in the form of small droplets.

The term "polyunsaturated fatty acid or ester thereof" as used herein means a fatty acid with two or more carbon-carbon double bonds in its hydrocarbon chain or the ester of such an acid.

The term "highly unsaturated fatty acid or ester thereof" as used herein means a polyunsaturated fatty acid having at least 18 carbon atoms and at least 3 double bonds or the ester of such an acid.

The term "fish oil" as used herein means oil or fat extracted from an animal living in water including but not limited to fish. Examples include, but are not limited to, oil or fat extracted from tuna, herring, mackerel, sardine, salmon, cod liver, anchovy, halibut and shark and combinations thereof.

The term "omega-3 fatty acid" as used herein means a polyunsaturated fatty acid whose first double bond occurs at the third carbon-carbon bond from the end opposite the acid group.

The term "comprising" as used herein means "consisting at least in part". That is to say when interpreting statements in this specification which include that term, the features prefaced by that term in each statement all need to be present but other features can also be present.

The term "%" unless otherwise defined means % w/w, i.e., the percentage measured in weight per total weight.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

5.2 The Emulsions of the Invention

The invention relates to an oil-in-water emulsion comprising droplets of a core lipid coated with nanoemulsion droplets, wherein the nanoemulsion droplets comprise a surface lipid coated with protein.

More particularly, the invention relates to an oil-in-water emulsion comprising droplets of fish oil coated with nanoemulsion droplets, wherein the nanoemulsion droplets comprise a lipid that is solid or partially solid at room temperature, which is coated with a milk protein.

The unique structural arrangement of the particles making up the emulsion confers advantageous properties on the emulsion of the invention.

Referring to FIG. 1, the emulsions of the invention comprise droplets (1) suspended in aqueous medium. The droplets (1) comprise a core lipid (2), which is coated with nanoemulsion droplets (3). Each nanoemulsion droplet (3) comprises a surface lipid (4) coated with protein (5). While FIG. 1 shows a few nanoemulsion droplets present on the surface of the core lipid, it should be appreciated that the nanoemulsion droplets surround the core lipid in three dimensions, thereby coating the core lipid.

The degree of coating depends on the relative amounts of the core lipid to nanoemulsion. Generally, most of the surface of the core lipid will be covered with nanoemulsion droplets, so as to encapsulate the core lipid in a matrix of nanoemulsion.

The nanoemulsion droplets as a whole, behave like large protein particles with their own innate emulsifying ability and the ability to be absorbed at the oil-water interface of the core lipid.

These protein-encapsulated droplets create a hydrophobic barrier around the core lipid which restricts diffusion of oxygen and water into the core lipid droplet, retarding oxidation. Hence the oxidative stability of the core lipid is increased.

The thick interfaced layer around the core lipid created by the nanoemulsion droplets helps to stabilise the emulsion so that it does not undergo coalescence during long storage periods.

The surface lipid of the nanoemulsion droplets is preferably solid or partially solid at room temperature. Oxidation of the core lipid may be further retarded by the solid or partially solid nature of the surface lipid in the nanoemulsion droplet as it is more difficult for oxygen and water molecules to diffuse through this layer, to reach the core lipid in the interior of the particle.

The oxidative stability of an oil-in-water emulsion can be increased by including antioxidants within the emulsion. Generally, the antioxidant will be mixed with the lipid to be protected. However, in the emulsions of the invention, antioxidants may be incorporated into the surface lipid so as to be located at the interface between the core lipid and the aqueous phase of the emulsion.

By targeting the antioxidants to the location where they are most effective, high oxidative stability can be achieved with a much smaller amount of antioxidant matter. In addition, locating the antioxidant in the surface lipid precludes any adverse chemical reactions between the antioxidant and the core lipid, or with other agents mixed with the core lipid.

The unique structure of the emulsions of the invention provides oxidative stability relative to simple emulsions prepared using the same proportions of the same lipids and proteins. In particular, the emulsions of the invention demonstrate very high heat stability, ie, they are oxidatively stable following heat treatment.

Oxidative stability can be measured using standard techniques in the art such as the TBARS determination, PV determination and propanal determination. The relative oxidative stability of two emulsions containing oxidisable lipids can be measured by comparing the results of one or more of these determinations.

In one embodiment the core lipid droplets have an average diameter of about 1000 nm to 100 μm, preferably 2 to 50 μm, more preferably 5 to 10 μm.

The core lipid droplets are coated with and stabilised by the nanoemulsion droplets which have an average diameter of about 50 to 1000 nm. Preferably the average diameter of the nanoemulsion droplets is 50 to 500 nm, more preferably, 50 to 200 nm.

In one embodiment, the nanoemulsion droplets coating the core lipid form a layer 50 to 500 nm thick, preferably 50 to 300 nm, more preferably 100 to 200 nm thick.

The average droplet size diameter can be measured using a particle size analyser such as the Malvern MasterSizer 2000 or similar device. The average droplet size diameter measured is the diameter of the droplet including the coating, ie the coating of nanoemulsion droplets around the core lipid, or the coating of protein around the surface lipid.

The emulsion of the invention may also comprise additives such as flavouring agents, nutrients, vitamins, stabilisers, preservatives, antioxidants, sweeteners, colouring agents, masking agents, sugars, buffers, disintegrating agents, suspending agents, solubilising agents, emulsifiers, enhancers and the like.

These additives may be present in the core or surface lipid, or in the aqueous phase of the emulsion.

5.3 The Core Lipid

The core lipid may be any lipid or mixture of lipids and is preferably an oxidisable lipid. An oxidisable lipid is a lipid that is at least partially oxidised by exposure to atmospheric oxygen. While it is recognised that all lipids can eventually be oxidised, some are more readily oxidisable than others. Unsaturated lipids are particularly vulnerable to spontaneous oxidation in the presence of oxygen.

The core lipid may be any lipid of use in the food, pharmaceutical or cosmetic industries and is preferably an edible lipid. The core lipid may be extracted from a marine animal, plant, phytoplankton or algae including microalgae, or any other appropriate source. Alternatively, it may be produced synthetically. The core lipid may be used in non-purified, purified or highly purified form, concentrated or non-concentrated.

Core lipids suitable for use in the invention include but are not limited to plant oils such as canola oil, borage oil, evening primrose oil, safflower oil, sunflower oil, flaxseed oil, wheat germ oil, algal oil, grapeseed oil; oxygen sensitive fats; and fish oils obtained from fish such as tuna, herring, mackerel, sardine, salmon, cod liver, anchovies, halibut and shark. Fish oils are generally high in LC PUFAs, in particular omega-3-fatty acids.

In one embodiment the core lipid comprises an oxidisable lipid. Preferably, the oxidisable lipid comprises a highly unsaturated fatty acid or ester thereof, such as an LC PUFA or ester thereof. In one embodiment, the core lipid is fish oil or is derived from fish oil. Most preferably, the core lipid comprises an omega-3 fatty acid, such as α-linolenic acid (ALA) eicosapentaenoic acid (EPA) or docosahexaenoic acid (DHA), or mixtures thereof.

In one embodiment the core lipid is a fish oil containing at least 10% of one or more LC PUFA, preferably at least 20%, more preferably 30%.

In one embodiment the core lipid may include fat soluble vitamins such as vitamins A, D, E and K; and/or other lipid soluble or lipid nutraceutical agent, for example; carotenoids (e.g. lutein, lycopene, zeaxanthin, Astaxanthin), phospholipids (e.g. phosphatidyl choline, phosphatidylinositol, and phosphatidyl ethanolamine), gangliosides, natural lipid appetite suppressants (such as stearoyl ethanolamide and oleyl ethanolamide), phytosterols (such as compesterol, stigmasterol and brassicasterol), limonene, lycopene, lutein, and the like.

In one embodiment the core lipid may include probiotics such as probiotic strains of *Lactococcus lactis, Lactobacillus bulganeus, Lactobacillus rhamnosus, Lactobacillus casie, Lactobacillus johnsonii, Lactobacillus plantarum, Bacillus coagulans, Lactobacillus acidophilus, Bifidobacterium infantis*, and the like.

5.4 The Surface Lipid

The surface lipid, when coated with a layer of protein, encapsulates and protects the core lipid particle or droplet.

In one embodiment the surface lipid is a lipid that is solid or partially solid at room temperature. Preferably the surface lipid is a non-oxidisable lipid, ie, a lipid not easily oxidised by atmospheric oxygen. More preferably the surface lipid is selected from the group comprising palm oil, anhydrous milk fat, coconut oil, cocoa butter and hydrogenated or partially hydrogenated vegetable oils such as soybean, rapeseed, sunflower, peanut, cottonseed, olive, corn, grape seed, safflower, sesame, ricebran and linseed oils.

The properties of the emulsion of the invention can be altered by changing the degree of solidification of the surface lipid. Hydrogenation of plant-based oils can be used to increase the melting point of the lipid.

In one embodiment the surface lipid may include lipid soluble flavour enhancers such as lemon oil.

5.5 The Protein

The protein encapsulates the surface lipid to make the nanoemulsion droplet.

In one embodiment, the protein is selected from the group comprising MPC, MPI, WPI, skim milk powder, whey protein, casein, sodium caseinate, calcium caseinate, soy protein, egg protein, or aggregates derived from these proteins, or mixtures thereof. Preferably, the protein is a milk protein, for example MPC, MPI, WPI, skim milk powder, whey protein, casein, sodium caseinate, calcium caseinate.

Preferably, the concentration of the protein solution that is homogenised with the surface lipid is high enough to ensure that substantially all of the surface lipid is protein coated. If too much protein is present, excess protein will remain in the dispersion phase of the emulsion.

The casein for use in the invention may be any casein protein including but not limited to α-casein, κ-casein, and β-casein, and their salts and mixtures thereof. Preferably, the casein is calcium or sodium caseinate.

The whey protein for use in the invention may be any milk serum protein or protein composition including but not limited to whey protein isolate, whey protein concentrate, α-lactalbumin and β-lacoglobulin. Preferably the whey protein is WPI.

In one embodiment the protein comprises protein aggregates of 50 nm to 1000 nm, preferably 100 nm to 500 nm, more preferably 200 nm to 300 nm. Proteins such as calcium caseinate are naturally present as aggregates. In other cases, aggregation or increased aggregation may be induced by acidification, addition of ions such as calcium, shearing, heat treatment, high pressure treatment, or a combination of these treatments. Methods of protein aggregation are well-known in the art.

5.6 Methods of Making the Emulsion of the Invention

The invention also provides a method of making an emulsion of the invention comprising (a) homogenising a surface lipid with a solution of protein to produce a nanoemulsion comprising droplets of the surface lipid coated with protein, and (b) homogenising the nanoemulsion with a core lipid to produce an emulsion comprising droplets of core lipid coated with nanoemulsion droplets, wherein the nanoemulsion droplets comprise the surface lipid coated with protein.

Optionally, the aqueous protein solution is heated with the surface lipid prior to homogenisation in step (a). In one embodiment, the protein solution and surface lipid are heated at 30 to 60° C. Heating may be required when the surface lipid has a high melting point such as palm oil.

In one embodiment a protein solution of concentration 0.5 to 6% is homogenised with a surface lipid in step (a). Preferably, the protein solution is of concentration 2 to 5%, more preferably 4%. Generally the protein solution and surface lipid are mixed in a ratio of 4:1 to produce a nanoemulsion of 20% surface lipid. The protein content of the nanoemulsion depends on the concentration of protein in the protein solution, and the ratio of protein solution to surface lipid homogenised.

Homogenisation may be performed using any device known in the art.

In one embodiment, the protein solution and surface lipid are homogenised at a pressure of 10 to 300 MPa, preferably 300 MPa. Higher pressure homogenisation results in a smaller average diameter of nanoemulsion droplet, as demonstrated in Example 3.

The nanaoemulsion is then mixed with the core lipid, and homogenised to form the emulsion of the invention in step (b). The ratio of nanoemulsion to core lipid can be altered to produce emulsions of the invention with different properties. For example 200 g core lipid added to 800 g nanoemulsion (20% surface lipid) provides an emulsion of the invention comprising 20% core lipid and 16% surface lipid.

To reduce the relative amount of surface lipid (and hence protein) the nanoemulsion can be mixed with water before homogenisation with the core lipid.

Optionally, the method includes a further step of deodorisation. In one embodiment the emulsion can be deodorised by bubbling nitrogen through it at reduced pressure.

Optionally, the method includes a further step of drying the emulsion. In one embodiment the emulsion can be dried by spray-drying to produce a powder. In another embodiment, the emulsion can be freeze-dried.

Optionally, the method includes a further step of heat treating or sterilisation. In one embodiment the emulsion is sterilised by ultra-high temperature (UHT) (e.g. 140° C. for 5 seconds). In another embodiment the emulsion is pasteurised (e.g. 72° C. for 15 seconds). In another embodiment the emulsion is retorted (e.g. heated in a sealed container at 120° C. for 20 minutes).

5.7 Uses of the Emulsion of the Invention

Foods containing oxidisable lipids such as omega-3 LC PUFA and esters are considered to be high value, functional foods. The emulsions and powders made in accordance with this invention are suitable as ingredients for use in a variety of foodstuffs including but not limited to milk and milk based products, dips, spreads, sauces, pastes, yogurts, condiments, dressings, beverages, pasta products, bread and bakery products, meat and fish products, infant foods, processed cheese, natural cheese, vegetable juice, fruit juice, sausage, pâte, candy, mayonnaise, dressing, soy bean sauce, soy bean paste. They may also used as an alternative source or partial replacement of oils and fats in ice cream, dairy dessert, creamers, soup bases, filled dairy products, snack foods and nutrition and sports bars.

The emulsion of the invention has the advantage that it is heat stable which allows it to be sterilised. For example, the high heat stability demonstrated by the emulsions of the invention allows them to be added to yogurt culture before heat-treatment and fermentation. This is hugely advantageous as it facilitates production of fortified yogurt without the need for any changes to be made to the production line. Typically, fortification with an oxidisable lipid such as fish oil would necessitate special equipment and processing steps, to ensure the lipid did not become rancid during the process, thereby tainting the yogurt. This is of great benefit as it allows the encapsulated lipid to be added to foods and nutriceutical products that must be sterilized before consumption, such as infant formula and UHT drinks.

The emulsion of the invention can also be used in other fields, such as to encapsulate oil-soluble flavours, antioxidants and other bioactives for medical uses. For example, nutraceuticals such as cod liver oil, mineral oil, oil-soluble vitamins and drugs delivered in an oil base can all be incorporated into the emulsion of the invention. In particular, the emulsion of the invention can be used to deliver vitamin A (retinol), vitamin D (calciferol), vitamin E (tocopherols, tocotrienols, vitamin K (quinone), beta-carotene (pro-vitamin-A) and combinations thereof.

The emulsions of the invention can also be used in the production of cosmetics such as moisturiser, skin cream, hand cream, face cream, massage cream or make-up.

The emulsion of the invention provides a convenient and cost effective means for stabilizing oxidisable lipids, such as fish oils. Encapsulation in a lipid/protein complex reduces the rate of oxidation of the oxidisable lipid and ensures that any offensive smell and/or taste is masked making it more palatable to consumers. In addition, the complex structure of the emulsion increases its stability, making it useful in products requiring a long shelf life.

Various aspects of the invention are illustrated by non-limiting ways by reference to the following examples.

6. EXAMPLES

Milk protein concentrates (MPCs), skim milk powder (SMP) and anhydrous milk fat (AMF) were supplied by the Fonterra Co-operative Group Limited, New Zealand. Palm oil (Palm Olein oil) was purchased from Davis Trading Co., Palmerston North, New Zealand. High melting point vegetable oil was obtained from Bakels Edible Oils Ltd (Palm stearine oil) Sunflower oil was purchased from Davis Trading Company, Palmerston North, New Zealand. Tuna fish oil (RoPUFA '30' n-3 food oil) was obtained from Roche Vitamins (UK) Ltd and used in Examples 1-10. Fish oil for use in Examples 11-14 was obtained from Maruha Nichiro Food Inc (EPA28SPE) and contained 28% EPA and 11% DHA.

All the chemicals used were of analytical grade and were obtained from either BDH Chemicals (BDH Ltd., Poole, England) or Sigma Chemical Co. (St. Louis, Mo.) unless specified otherwise.

Example 1

Preparation of Emulsion of the Invention

MPC dispersions were prepared by adding MPC powder to Milli-Q water (water purified by treatment with a Milli-Q apparatus; Millipore Corp., Bedford, Mass.) and then stirring for 60 min at room temperature to ensure complete dispersion. The pH of the dispersions was adjusted in the range 6.8-7.0.

Appropriate quantities of palm oil were then mixed with protein solutions of different concentrations to give 20% palm oil in the nanoemulsion. For example, 200 g palm oil mixed with 800 g protein solution gave a 20% palm oil nanoemulsion. The mixture of MPC dispersion and palm oil was heated to 60° C. and then homogenized in a Microfluidizer at a pressure of 300 MPa to form a nanoemulsion. The nanoemulsion comprised 20% surface lipid and 80% protein solution. The nanoemulsion droplets were in a range of 50 to 200 nm average diameter.

Appropriate quantities of fish oil were mixed with the nanoemulsion to give 20% fish oil and between 2 to 16% palm oil in the final emulsion, i.e. the ratio of nanoemulsion to core lipid was varied. For example, 200 g fish oil added to 800 g of nanoemulsion containing 20% palm oil provides an emulsion of the invention comprising 16% palm oil. 200 g fish oil mixed with 400 g nanoemulsion (20% palm oil) and 400 g water gives a nanoemulsion of the invention comprising 8% palm oil. As the relative amount of nanoemulsion decreases, so does the amount of palm oil and protein in the final product.

The mixture of the fish oil and nanoemulsion was homogenized in a homogenizer or using a laboratory high-speed mixer (10000 rev·min$^{-1}$ for 2 min) (Diax 600, Heidolph, Germany).

The process is shown diagrammatically in FIG. 2.

Example 2

Droplet Size of Nanoemulsions Prepared Using Different Protein Concentrations

Nanoemulsions were prepared using. MPC solutions of differing concentration and palm oil as described in Example 1. The particle or droplet size of the nanoemulsion was measured using a Malvern MasterSizer 2000 (Malvern Instruments Ltd, Malvern, Worcestershire, UK).

Droplet size measurements are reported as average diameters, $d_{32}$. The $d_{32}$ is defined as $\Sigma n_i d_i^3 / \Sigma n_i d_i^2$, where $n_i$ is the number of particles with diameter $d_i$. Mean particle diameters were calculated as the average of duplicate measurements. The relative refractive index (N), i.e., the ratio of the refractive index of the nanoemulsion droplets (1.456) to that of the dispersion medium (1.33), was 1.095. The absorbance value of the emulsion droplets was 0.001.

The average diameter of the nanoemulsion droplets decreased with an increase in the concentration of protein in the protein solution used, up until a solution concentration of 4% w/w as shown in FIG. 3. The size remained constant when the concentration of the solution was higher than 4%. This indicates that a protein solution of 4%, when used to form a nanoemulsion, is sufficiently concentrated to fully cover the nanodroplet. If the protein concentration is higher than 4% this may result in some unadsorbed protein being present in the aqueous phase.

Example 3

Droplet Size of Nanoemulsions Prepared Using Different Homogenisation Pressures 80 g of 4% (w/w) MPC solution and 20 g palm oil were homogenised to form a nanoemulsion (20% palm oil) using a microfludizer at different pressure. The average droplet size of the nanoemulsions decreased from ~0.19 μm to ~0.13 μm when the pressure used was increased from 100 MPa to 300 MPa as shown in FIG. 4:

Example 4

Droplet Size of Emulsions of the Invention Prepared Using Different Proportions of Nanoemulsion Emulsions of the invention were prepared as described in Example 1. First nanoemulsions were prepared using 4% (w/w) MPC solution and palm oil homogenised at 300 MPa. The nanoemulsions comprised 80% protein solution and 20% palm oil.

Fish oil was then homogenised with the nanoemulsion in different proportions to give an emulsion of the invention comprising 20% fish oil and from 2 to 16% palm oil (w/w).

The average diameter size of the emulsion droplets (the nanoemulsion-coated droplets of core lipid) decreased with increasing relative amount of nanoemulsion. As there are no other emulsifying agents in the system, this suggests that the nanoemulsion is playing a role as an emulsifying agent in the formation of the emulsions of the invention. The results are shown in FIG. 5.

Example 5

Confocal Laser Scanning Microscopy of Emulsions of the Invention

The microstructures of the emulsions of the invention were observed by confocal laser scanning microscopy (CLSM).

A Leica (Heidelberg, Germany) confocal laser scanning microscope with a chosen objective lens and an Ar/Kr laser with an excitation line of 488 nm (in such a way that only the fluorescent wavelength band could reach the detector system) was used to determine the microstructure of the emulsions. Emulsions were prepared as described in Example 1. Approximately 3 mL of sample was taken in a test tube, nile blue (fluorescent dye) was mixed through, and then the mixture was placed on a microscope slide. The slide was covered with a coverslip and observed under the microscope.

The micrographs are shown in FIG. 6 where it can be seen that the nanoemulsion droplets are adsorbed at the surface of the droplets of the core lipid. The nanoemulsion droplets build a thick surface layer coating on the droplets of the core lipid. The thickness of the surface layer is >200 nm, which is 10-20 times thicker than the protein monolayer encapsulating the surface lipid in the nanoemulsion droplets.

Example 6

Lipid Oxidation of the Emulsion

Lipid oxidation of the fish oil emulsion of the invention and two control emulsions was examined using gas chromatography (GC).

Emulsions of the invention were prepared according to Example 1 using fish oil homogenised with a nanoemulsion comprising 4% (w/w) MPC solution and palm oil. The final concentrations in the emulsion were 10% (w/w) palm oil, 20% (w/w) fish oil and 2% (w/w) MPC.

Control 1 (mix) was prepared by mixing palm oil, fish oil and MPC ingredients together with Silverson Homogeniser at 6400 rpm for 2 min. The final concentration of Control 1 emulsion was 10% palm oil, 20% fish oil and 2% MPC. This simple emulsion contained the same elements of the emulsion of the invention but not the structure.

Control 2 (fish oil) was prepared by mixing fish oil and MPC solution together with a Silverson Homogeniser at 6400 rpm for 2 min. The final concentrations in the emulsion were 20% (w/w) fish oil and 2% (w/w) MPC.

3 ml of the sample emulsion was transferred into a Supelco SPME sampling vial and flashed with oxygen. The cap was sealed immediately to keep the oxygen inside the vial to accelerate the oxidation. The vial was stored at 20° C. for the GC testing. The fibre was inserted into the headspace and the vials were incubated for 20 min at 50° C. The fibre was then transferred to the injector of a gas chromatograph. The direct injection model was used to maximize the sensitivity. The fiber was allowed to remain in the injector for a further 10 min to condition it for the next analysis.

Gas chromatography (GC) analyses were conducted on a Shimadzu model 2010 GC instrument fitted with a flame ionization detector (FID) and a Restek fused silica capillary column (30 m, 0.25 mm i.d., 1 μm film, Biolab, Palmerston North, New Zealand). Helium was used as the carrier gas at a constant linear velocity of 20 cm s$^{-1}$. The temperatures of the injector and the FID detector were held at 250 and 260° C., respectively. The oven temperature was initially held at 60° C. for 10 min before being increased to 150° C. at 60° C. Propanal was identified by its retention time and was confirmed using a chemical standard under the same operating conditions.

As shown in FIG. 7, over a short storage time (<23 h) the three samples did not produce markedly different amounts of propanal. However, more propanal was produced from the two control samples when the samples were stored for 47 h. The difference in the amount of propanal produced by emulsion of the invention (nano) and control samples (mix and fish) was more significant after the longer storage time. This suggests that there is less oxidation of fish oil in the emulsion of the invention than in the control emulsion samples.

Example 7

Sensory Testing of Yogurt Fortified with the Fish Oil Emulsions of the Invention Yogurts fortified with omega-3 LC PUFA emulsions were evaluated by a sensory panel. The yogurts evaluated were
(a) control 1: yogurt containing no fish oil
(b) control 2: yogurt containing a simple emulsion of fish oil and MPC
(c) test: yogurt containing emulsions of the invention containing fish oil as the core lipid.

The emulsions were prepared in accordance with Example 6.

Samples of yogurt containing the fish oil emulsions of the invention and antioxidants were also tested. The antioxidants were added to the surface lipid during formation of the emulsion. The antioxidants used constituted 0.075% tocopherol and 0.05% ascobyl palmitate as a wt percentage of the final emulsion.

The sensory panel was selected based on the ability of the panelists to detect differences in "fishy" flavours. These panelists were well trained in sensory evaluation and were familiar with the test method used.

For evaluation by a sensory panel, 15-20 g of each yogurt sample was weighed into a 60 mL clear sample cup with a lid and was presented in a random order with three-digit coded numbers. A "difference from control" assessment method using a ten-point hedonic scale was applied: 0 indicated totally no fish taste in a sample, whereas 10 indicated that the sample was fish oily tasting and extremely different from the reference.

At each evaluation, a maximum of six samples, together with one reference (control 1) and one blind control (control 2 or test sample), were presented to the panelists. All yogurt samples were stored at 4° C. for 4 weeks and assessment was carried out at the end of week 1 and again at the end of week 4.

The results show the yogurt containing the emulsion of the invention did not have significant fishy taste or odour after a storage time of 4 weeks, whereas the yogurts containing the control 2 fish oil emulsion had a significant fishy taste or odour (Table 1).

TABLE 1

Sensory testing results of yogurt containing the fish oil.

| Sample | 0 week | 1 week | 2 weeks | 3 weeks | 4 weeks |
|---|---|---|---|---|---|
| Yogurt (Control 1) | $1.2^a \pm 0.40$ | $1.0^a \pm 0$ | $1.5^a \pm 0.50$ | $1.5^a \pm 0.55$ | $1.2^a \pm 0.45$ |
| Yogurt containing normal fish oil emulsion (control 2) (150 mg/serving) | $4.0^b \pm 3.03$ | $4.0^b \pm 1.41$ | $5.0^b \pm 2.45$ | $4.4^b \pm 3.05$ | $5.0^b \pm 2.34$ |
| Yogurt containing novel fish oil emulsion (test) (150 mg/serving) | $2.31^a \pm 0.40$ | $2.5^a \pm 1.26$ | $1.8^a \pm 1.10$ | $2.2^a \pm 1.10$ | $2.6^a \pm 1.95$ |
| Yogurt containing novel fish oil emulsion + antioxidants (test) (150 mg/serving) | $4.4^b \pm 1.02$ | $1.7^a \pm 0.75$ | $1.1^a \pm 0.23$ | $1.7^a \pm 1.10$ | $3.0^{ab} \pm 2.00$ |
| Yogurt containing normal fish oil emulsion (control 2) (200 mg/serving) | $3.6^b \pm 1.50$ | $4.8^b \pm 1.57$ | $3.6^b \pm 1.73$ | $4.8^b \pm 2.71$ | $3.4^b \pm 2.33$ |
| Yogurt containing novel-fish oil emulsion (test) (200 mg/serving) | $2.7^a \pm 0.87$ | $2.3^a \pm 0.94$ | $2.2^a \pm 1.30$ | $1.6^a \pm 0.65$ | $3.2^{ab} \pm 2.59$ |
| Yogurt containing novel-fish oil emulsion + antioxidants (test) (200 mg/serving) | $4.1^b \pm 1.20$ | $1.3^a \pm 0.47$ | $1.2^a \pm 0.45$ | $1.25^a \pm 0.50$ | $1.6^a \pm 0.58$ |

1 Responses input on a ten-point hedonic scale, where 0 = no difference from control and 10 = extremely different from control.
2 Data are means ± sample standard deviations. In a row or column, data followed by different letters are significantly different (P < 0.05). This calculation is done using Tukey's Pair wise comparison (HSD test).

Samples containing emulsions of the invention with antioxidants present in the surface lipid gave significantly better results.

Example 8

Formation of the Emulsions with MPC and Sunflower Oil Surface Lipid

4% (w/w) MPC and 20% sunflower oil (w/w) were homogenised to form nanoemulsions using a microfludizer at pressure of 200 MPa. Nanoemulsions of average droplet size of 100 nm to 200 nm were made.

The nanoemulsion with small average droplet size (about 100 nm) was used to process to further form the novel emulsions.

20 g fish oil was homogenised with a nanoemulsion made from sunflower oil mixed with 4% MPC solution (10% sunflower oil nanoemulsions). Homogenisation was in a laboratory high-speed mixer (10000 rev·min$^{-1}$ for 2 min) (Diax 600, Heidolph, Germany). The structures of the emulsions are shown in FIG. 8. It demonstrates the formation of the oil-in-water emulsion of the invention where the core lipid is coated with a surface layer formed by the nanoemulsion droplets made from MPC and sunflower oil.

Example 9

Formation of the Emulsions with MPC and Milk Fat Surface Lipid

4% (w/w) MPC and 20% anhydrous milk fat (AMF) (w/w) were homogenised to form nanoemulsions using a microfludizer at pressure of 20 KPa. The nanoemulsion with small droplet size (about 100 nm) was used to process to further form the novel emulsions. 20% fish oil and 10% nanoemulsions made with MPC and milk at were homogenized in a laboratory high-speed mixer (10000 rev·min$^{-1}$ for 2 min) (Diax 600, Heidolph, Germany). The structure of the emulsion is shown in FIG. 9. It demonstrates the formation of the emulsion of the invention with the surface layer formed from the nanoemulsion made with MPC and milk fat.

Example 10

Formation of the Emulsions of the Invention with Skim Milk Powder and Palm Oil Surface Lipid 15% (w/w) skim milk powder (SMP) and 20% palm oil (w/w) were homogenised to form the nanoemulsions using a microfludizer at pressure of 20 KPa. The nanoemulsion with small droplet size (about 100 nm) was used to process to further form the emulsions of the invention. 20% fish oil and 5% nanoemulsions made with SMP and palm oil were homogenized in a laboratory high-speed mixer (10000 rev·min$^{-1}$ for 2 min) (Diax 600, Heidolph, Germany). The structure of the emulsion is shown in FIG. 10. It demonstrates the formation of the emulsion of the invention with the surface layer formed from the nanoemulsion made with SMP and palm oil.

Example 11

Lipid Oxidation of Fish Oil Emulsions of the Invention

Lipid oxidation in the fish oil emulsion of the invention and the corresponding control emulsion were examined using lipid hydroperoxide value (PV), thiobarbituric acid reactive substances testing (TBARS), and gas chromatography (GC).

Emulsions of the invention were prepared according to Example 1 using fish oil (EPA28SPE) homogenised with a nanoemulsion comprising 4% (w/w) MPC solution and a surface lipid. The final concentrations in the emulsion were 10% (w/w) surface lipid, 20% (w/w) fish oil and 2% (w/w) MPC. Three different surface lipids—palm oil, high melting point milk fat, and high melting point vegetable oil, were used to make the nanoemulsions.

Control emulsions were prepared by mixing surface lipid, fish oil and MPC ingredients together with Silverson Homogeniser at 6400 rpm for 1 min to form a coarse emulsion. The coarse emulsions were then passed through a 2-stage high pressure valve homogeniser (APV 1000, APV 4B George Bourke Drive, Mt Wellington, Auckland, New Zealand) a single time to reduce the mean particle diameter at 150/50 bars. The final concentration of the control emulsion was 10% surface lipid, 20% fish oil and 2% MPC. This emulsion contained the same elements of the emulsion of the invention but not the same structure.

Methods of Lipid Oxidation 3 ml of the sample emulsion was transferred into a Supelco SPME sampling vial and flushed with oxygen. The cap was sealed immediately to keep the oxygen inside the vial to accelerate the lipid oxidation. The vial was stored at 20° C. for the GC testing. At end of storage time, the vial was opened and the emulsion sample was taken from the vial for PV and TBARS testing.

Thiobarbituric Acid Reactive Substances (TBARS) Determination

TBARS were determined by mixing 0.5 ml of emulsion with 2.0 ml of TBARS reagent (immediately used after mixing equal amount of freshly prepared 0.025 M thiobarbituric acid in 0.2 M NaOH solution and 2M HPO/2M Citric acid) in a test tube and placing the test tube into boiling water for 10 min (Hegenauer, J., Saltman, P., Ludwig, D., Ripley, L., & Bajo, P. (1979) Effects of supplemental iron and copper on lipid oxidation in milk. 1. Comparison of metal complex in emulsified and homogenised milk. *Journal of Agricultural & Food Chemistry*, 27, 860-867).

After heating, the tubes were cooled to room temperature and 3 ml of cyclohexanone was added. The tubes were vortexed 3 times for 10 s and then centrifuged (1000×g) for 5 min. The top layer contains TBARS which were measured at 532 nm. The concentrations of TBARS were determined using a standard curve prepared using 1,1,3,3-tetraethoxypropane (Elias, R. J., Bridgewater, J. D., Vachet, R. W., Waraho, T., McClements, D. J., & Decker, E. A. (2006). Antioxidant mechanisms of enzymatic hydrolysates of blactoglobulin in food lipid dispersions. *Journal of Agricultural and Food Chemistry*, 54, 9565-9572).

Lipid Hydroperoxides Value (PV) Determination

Lipid hydroperoxides were determined using a method adapted from Shantha and Decker (Shantha, N. C., & Decker, E. A. (1994). Rapid, sensitive, ion-based spectrophotometric methods for determination of peroxide values of food lipids. *Journal of AOAC International*, 77, 421-424) and Nuchi et al. (2001).

Emulsion (0.5 ml) was mixed with 2.5 ml of an effective extraction solvent (ethanol/ethyl acetate/n-hexane, 1:1:1 (v/v/v)) and left thawing at room temperature for 20 min. The solvent mixture had been formerly used successfully by Satue-Gracia et al (Satue-Gracia, M. T., Frankel, E. N., Rangavajhyala, N., & German J. B. (2000). Lactoferrin in infant formulas: Effect on oxidation. *Journal of Agricultural and Food Chemistry*, 48, 4984-4990) to extract fat from infant formulas. A votexing procedure to extract the lipids from the samples and a centrifugation step followed. Supernatant (0.2 ml) was transferred to a reaction tube with 4 ml of methanol/butanol (2:1(v/v)).

Ammonium thiocyanate 25 µl (3.94 M) and ferrous ion solution 25 µl (prepared by mixing 0.132M $BaCl_2$ and 0.144 M $FeSO_4$) were added. After each addition, the reaction tubes were votexed for 10 seconds. The tubes were then kept in the dark at room temperature for 20 min. The absorbance at 510 nm was measured using a Genesys 10UV Scanning spectrophotometer (Thermo Fisher Scientific, 12C Rennie Drive, Auckland, New Zealand). The concentration of lipid hydroperoxides was calculated from a cumene hydroperoxide standard curve.

Propanal Determination 3 ml of the sample emulsion was transferred into a Supelco SPME sampling vial and flashed with oxygen. The cap was sealed immediately to keep the oxygen inside the vial to accelerate the oxidation. The vial was stored at 20° C. for the GC testing. The fibre was inserted into the headspace and the vials were incubated for 20 min at 50° C. The fibre was then transferred to the injector of a gas chromatograph. The direct injection model was used to maximize the sensitivity. The fiber was allowed to remain in the injector for a further 10 min to condition it for the next analysis.

Measurements of propanal by static headspace solid phase microextraction (HS-SPME) gas chromatography is described in Iglesias, J., Lois, S., Medina, I. (2007). Development of a solid-phase microextraction method for determination of volatile oxidation compounds in fish oil emulsions. *Journal of Chromatography A*. 1163, 277-287 the measurements were carried out using a Shimadzu GC-2010 with AOC-5000 Headspace auto sampler (Shimadzu Scientific Instruments (Oceania) PTY. LTD., Unit A, Collard Place, Lincoln, New Zealand) coupled with a flame ionization detector (FID) and a Restek fused silica capillary column (30 m, 0.25 mm i.d., 1 µm film, Biolab, Palmerston North, New Zealand). Helium was used as the carrier gas at a constant linear velocity of 20 cm $s^{-1}$. The temperatures of the injector and the FID detector were held at 250 and 260° C., respectively. The oven temperature was initially held at 60° C. for 10 min before being increased to 150° C. at 60° C. $min^{-1}$. Propanal was identified by its retention time and was confirmed using a chemical standard under the same operating conditions.

Results

Lipid hydroperoxides values (PV) of both control sample and emulsions of the invention (nanoemulsion) increased with the storage time (FIG. 11). The PV results of the emulsions of invention made with all three different surface lipids were significantly lower than the PV results of the corresponding control emulsions.

TBARS results of both control sample and emulsions of invention increased with the storage time (FIG. 12). The TBARS results of the emulsions of invention made with all three different surface lipids were significantly lower than the TBARS results of the corresponding control emulsions.

Propanal results of both control sample and emulsions of invention increased with the storage time (FIG. 13). The propanal results of the emulsions of invention made with palm oil and high melting point vegetable oil as surface lipids were significantly lower than the propanal results of the corresponding control emulsions.

As shown in FIG. 11-13, the PV values, TBARS and Propanal values indicate that the fish oil emulsions of the invention have better anti-oxidation properties compared to control samples that were formed using the same protein and lipid composition. Furthermore, emulsions of the invention formed by the high melting vegetable oil has the best anti-oxidation properties, suggesting that the nanoemulsion coating the fish oil droplets has better anti-oxidant properties when formed with high melting point oil (solid particles at room temperature). As the melting temperature decreases, high melting vegetable oil>palm oil>milk fat the anti-oxidant properties decrease too.

Example 12

Sensory Testing of Laboratory Prepared Yogurt Fortified with Fish Oil Emulsions of the Invention (Palm Oil as Surface Lipid)

Yogurts fortified with omega-3 LC PUFA were evaluated by a sensory panel. The yogurts evaluated were:
(a) control: yogurt containing a simple emulsion of fish oil and MPC
(b) test: yogurt containing emulsions of the invention containing fish oil as the core lipid.

Samples of yogurt containing (a) the fish oil emulsions of the invention prepared in accordance with Example 11, and (b) a simple emulsion were added to laboratory prepared yogurt. The emulsion was added to the milk after heat treatment (HT 90° C. for 5 mins) and before fermentation (40° C. for 6 to 8 hours). The ingredients used for the yogurt are as in Table 2:

TABLE 2

Ingredients of yogurt fortified with fish oil using an emulsion of the invention (palm oil as surface lipid) and a simple emulsion

| Test emulsion | | Simple emulsion | |
|---|---|---|---|
| Milk with 1.5% Fat | 1455 g | Milk with 1.5% Fat | 1455 g |
| Skim milk powder | 45 g | Skim milk powder | 45 g |
| Culture | 30 g | Culture | 30 g |
| Test emulsion | 25.833 g | Simple emulsion | 25.833 g |

The sensory panel was selected based on the ability of the panelists to detect differences in "fishy" flavours. These panelists were well trained in sensory evaluation and were familiar with the test method used.

For evaluation by a sensory panel, 15-20 g of each yogurt sample was weighed into a 60 mL clear sample cup with a lid and was presented in a random order with three-digit coded numbers. A "difference from control" assessment method using a ten-point hedonic scale was applied: 0 indicated totally no fish taste in a sample, whereas 10 indicated that the sample was fish oily tasting and extremely different from the reference.

At each evaluation, control and test sample were presented to the panelists. All yogurt samples were stored at 4° C. for 4 weeks and assessments were carried out at day 0, the end of week 1, and continue at end of each week until the end of week 4.

The results show the yogurt containing the emulsion of the invention did not have significant fishy smell at storage time (4 weeks), whereas the yogurts containing the simple fish oil emulsion had a significant fishy smell (Table 3).

TABLE 3

Sensory testing results of yogurt containing the fish oil

| Sample | Day 0 | Week 1 | Week 2 | Week 3 | Week 4 |
|---|---|---|---|---|---|
| Control | 5.25 ± 1.5 | 3.8 ± 1.6 | 4.4 ± 1.7 | 4.8 ± 2.2 | 5 ± 2.2 |
| Test | 3.75 ± 1.5 | 2.6 ± 0.9 | 2 ± 0 | 1.8 ± 0.8 | 1.8 ± 0.8 |

[1]Responses input on a ten-point hedonic scale, where 0 = no fishy flavour and 10 = extremely fishy. A score below 2 indicates the person is willing to buy the product from supermarket. A score above 3 indicates the person is not willing to buy the product from supermarket because of the fishy flavour.
[2]Data are means ± sample standard deviations.

Example 13

Sensory Testing of Laboratory Prepared Yogurt Fortified with Fish Oil Emulsions of the Invention (High Melting Point Vegetable Oil as Surface Lipid)

Yogurts fortified with omega-3 LC PUFA were evaluated by a sensory panel. The yogurts evaluated were:
(a) control: yogurt containing a simple emulsion of fish oil and MPC
(b) test: yogurt containing emulsions of the invention containing fish oil as the core lipid.

Samples of yogurt containing the (a") fish oil emulsions of the invention prepared in accordance with Example 11, and (b) a simple emulsion were added to laboratory prepared yogurt. Each emulsion was added to the milk before heat treatment (HT 90° C. for 5 mins) and fermentation (40° C. for 6 to 8 hours). The ingredients used for the yogurt are as in Table 4:

TABLE 4

Ingredients of yogurt fortified with fish oil using emulsions of the invention (high melting point vegetable oil as surface lipid) and simple emulsion

| Test emulsion | | Simple emulsion | |
|---|---|---|---|
| Milk with 1.5% Fat | 1455 g | Milk with 1.5% Fat | 1455 g |
| Skim milk powder | 45 g | Skim milk powder | 45 g |
| Culture | 30 g | Culture | 30 g |
| Test emulsion | 20.833 g | Simple emulsion | 20.833 g |

The sensory panel was selected based on the ability of the panelists to detect differences in "fishy" flavours. These panelists were well trained in sensory evaluation and were familiar with the test method used.

For evaluation by a sensory panel, 15-20 g of each yogurt sample was weighed into a 60 mL clear sample cup with a lid and was presented in a random order with three-digit coded numbers. A "difference from control" assessment method using a ten-point hedonic scale was applied: 0 indicated totally no fish taste in a sample, whereas 10 indicated that the sample was fish oily tasting and extremely different from the reference.

At each evaluation, control and test sample were presented to the panelists. All yogurt samples were stored at 4° C. for 4 weeks and assessments were carried out at day 1, the day 12, day 21, and day 28.

The results show the yogurt containing the emulsion of the invention did not have significant fishy smell at storage time (4 weeks), whereas the yogurts containing the simple fish oil emulsion had a significant fishy smell (Table 5).

TABLE 5

Sensory testing results of yogurt containing the fish oil

| Sample | Day 1 | Day 12 | Day 21 | Day 28 |
|---|---|---|---|---|
| Control | 3.7 ± 1.0 | 3.6 ± 1.1 | 3.2 ± 1.3 | 3.2 ± 1.6 |
| Test | 1.5 ± 0.5 | 1.5 ± 0.9 | 1.6 ± 0.6 | 1.7 ± 0.8 |

[1]Responses input on a ten-point hedonic scale, where 0 = no fishy flavour and 10 = extremely fishy. A score below 2 indicates the person is willing to buy the product from supermarket. A score above 3 indicates the person is not willing to buy the product from supermarket because of the fishy flavour.
[2]Data are means ± sample standard deviations.

Example 14

Flavoured Emulsions Fortified with the Fish Oil Emulsions of the Invention (Palm Oil as Surface Lipid)

Flavoured emulsions fortified with omega-3 LC PUFA were evaluated by a sensory panel. The flavoured emulsions evaluated were:
(a) control: flavoured emulsion containing a simple emulsion of fish oil and MPC
(b) test: flavoured emulsion containing emulsions of the invention containing fish oil as the core lipid.

The ingredients to be used for the flavoured emulsions are as in Table 6.

TABLE 6

Ingredients of flavoured emulsion fortified with fish oil using emulsions of the invention (palm oil as surface lipid) and simple emulsion

| Test | | Control | |
|---|---|---|---|
| Test emulsion | 45.5 g | Simple emulsion | 45.5 g |
| Sugar | 15 g | Sugar | 15 g |
| Xanthan solution (0.5%) | 4 g | Xanthan solution (0.5%) | 4 g |
| Citric acid (25%) | 2.3 g | Citric acid (25%) | 2.3 g |
| Lemon flavour | 0.8 g | Lemon flavour | 0.8 g |
| Colour | 4 drops | Colour | 4 drops |
| K Ascorbate | 0.05 g | K Ascorbate | 0.05 g |
| Na Erythorbate | 0.025 g | Na Erythorbate | 0.025 g |

The sensory panel was selected based on the ability of the panelists to detect differences in "fishy" flavours. These panelists were well trained in sensory evaluation and were familiar with the test method used.

For evaluation by a sensory panel, 15-20 g of each flavoured emulsion sample was weighed into a 60 mL clear sample cup with a lid and was presented in a random order with three-digit coded numbers. A "difference from control" assessment method using a ten-point hedonic scale was applied: 0 indicated totally no fish taste in a sample, whereas 10 indicated that the sample was fish oily tasting and extremely different from the reference.

At each evaluation, control and test sample were presented to the panelists. All flavoured emulsion samples were stored at 25° C. for 4 weeks and assessments were carried out at day 1, day 3, day 7, and the end of week 4.

The results show the flavoured emulsion containing the emulsion of the invention did not have significant fishy smell at storage time (4 weeks), whereas the yogurts containing the control fish oil emulsion had a significant fishy smell (Table 7).

TABLE 7

Sensory testing results of yogurt containing the fish oil

| Sample | 1 day | 3 days | 7 days | 4 weeks |
|---|---|---|---|---|
| control | 2 ± 1.0 | 2.6 ± 1.1 | 2.8 ± 1.1 | 2.8 ± 1.0 |
| test | 1.6 ± 0.9 | 1.6 ± 0.9 | 1.4 ± 0.5 | 1.6 ± 0.6 |

[1]Responses input on a ten-point hedonic scale, where 0 = no fishy flavour and 10 = extremely fishy. A score below 2 indicates the person is willing to buy the product from supermarket. A score above 3 indicates the person is not willing to buy the product from super market because of the fishy flavour.
[2]Data are means ± sample standard deviations.

7. INDUSTRIAL APPLICATION

The emulsions of the present invention have utility in the food industry. They can be used to protect oxidisable lipids such as omega-3 fatty acids from oxidative damage.

The emulsions of the present invention can be incorporated into food products and/or cosmetics, preventing or reducing oxidation of the oxidisable lipid, thereby increasing product shelf life.

Those skilled in the art will understand that the above description is provided by way of illustration only and that the invention is not limited thereto.

The invention claimed is:

1. An oil-in-water emulsion comprising droplets of a core lipid coated with nanoemulsion droplets, wherein the nanoemulsion droplets comprise a surface lipid coated with protein, and wherein the surface lipid is a lipid that is solid or partially solid at room temperature.

2. The emulsion of claim 1 wherein the core lipid comprises an oxidisable lipid.

3. The emulsion of claim 1 wherein the core lipid comprises a LC PUFA or ester thereof.

4. The emulsion of claim 3 wherein the core lipid comprises an omega-3 fatty acid, α-linolenic acid (ALA), eicosapentaenoic acid (EPA) or docosahexaenoic acid (DHA), or combination thereof.

5. The emulsion of claim 3 wherein the core lipid comprises a fish oil.

6. The emulsion of claim 1 wherein the surface lipid is selected from the group comprising palm oil, anhydrous milk fat, coconut oil, cocoa butter and hydrogenated or partially hydrogenated vegetable oils selected from soybean, rapeseed, sunflower, peanut, cottonseed, olive, corn, grape seed, safflower, sesame, rice bran, and linseed oils, or mixtures thereof.

7. The emulsion of claim 6 wherein the surface lipid is selected from the group comprising one or more of palm oil, hydrogenated or partially hydrogenated vegetable oil and anhydrous milk fat.

8. The emulsion of claim 1 wherein the protein is selected from the group comprising MPC, MPI, WPI, whey protein, skim milk powder, casein, sodium caseinate, soy protein, egg protein, calcium caseinate or aggregates derived from these proteins or mixtures thereof.

9. The emulsion of claim 8 wherein the protein is a milk protein.

10. The oil-in-water emulsion of claim 1 comprising droplets of fish oil coated with nanoemulsion droplets, wherein the nanoemulsion droplets comprise a lipid that is solid or partially solid at room temperature, which is coated with a milk protein.

11. The oil-in-water emulsion of claim 1 comprising droplets of fish oil coated with nanoemulsion droplets, wherein the nanoemulsion droplets comprise a surface lipid selected from the group comprising one or more of palm oil, hydrogenated or partially hydrogenated vegetable oil or anhydrous milk fat, the surface lipid being coated with a milk protein.

12. A method of making an emulsion of claim 1 comprising
 (a) homogenising a surface lipid with a solution of protein to produce a nanoemulsion comprising droplets of the surface lipid coated with protein,
 (b) homogenising the nanoemulsion with a core lipid to produce an emulsion comprising droplets of core lipid coated with nanoemulsion droplets,
 wherein the nanoemulsion droplets comprise the surface lipid coated with protein, and wherein the surface lipid is a lipid that is solid or partially solid at room temperature.

13. The method of claim 12 wherein the core lipid is a fish oil.

14. A food or cosmetic product comprising an emulsion of claim 1.

15. The food product of claim 14 that is a dairy product.

* * * * *